US012761214B2

(12) United States Patent
Aburaya et al.

(10) Patent No.: US 12,761,214 B2
(45) Date of Patent: Oct. 13, 2026

(54) IMMUNOCHROMATOGRAPHY

(71) Applicant: FUJIFILM Corporation, Tokyo (JP)

(72) Inventors: Yoshihiro Aburaya, Ashigarakami-gun (JP); Junichi Katada, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 970 days.

(21) Appl. No.: 17/851,215

(22) Filed: Jun. 28, 2022

(65) Prior Publication Data

US 2022/0326227 A1 Oct. 13, 2022

Related U.S. Application Data

(63) Continuation of application No. PCT/JP2020/042911, filed on Nov. 18, 2020.

(30) Foreign Application Priority Data

Jan. 31, 2020 (JP) ................................ 2020-014454

(51) Int. Cl.
*G01N 33/543* (2006.01)
*G01N 33/531* (2006.01)
*G01N 33/53* (2006.01)

(52) U.S. Cl.
CPC ......... *G01N 33/531* (2013.01); *G01N 33/543* (2013.01)

(58) Field of Classification Search
None
See application file for complete search history.

(56) References Cited

U.S. PATENT DOCUMENTS

| | | | | |
|---|---|---|---|---|
| 2007/0037192 A1* | 2/2007 | Ziomek | .................... C07K 1/30 435/69.1 |
| 2014/0087367 A1 | 3/2014 | Wada | |
| 2018/0292398 A1 | 10/2018 | Wada et al. | |
| 2019/0126265 A1 | 5/2019 | Weigl et al. | |

FOREIGN PATENT DOCUMENTS

| | | | |
|---|---|---|---|
| JP | 2002-202307 A | 7/2002 |
| JP | 2003-28875 A | 1/2003 |
| JP | 5728453 B2 | 6/2015 |
| JP | 2018-84524 A | 5/2018 |
| WO | WO 2017/104143 A1 | 6/2017 |
| WO | WO 2019/186486 A1 | 10/2019 |

OTHER PUBLICATIONS

Thomas et al., Urine Collection and Processing for Protein Biomarker Discovery and Quantification, Cancer Epidemiol Biomarkers Prev; 19(4), Apgile 2010, pp. 953-959. (Year: 2010).*
Lin et al., Enrichment and separation of acidic and basic proteins using the centrifugal ultrafiltration followed by nanoparticle-filled capillary electrophoresis, Electrophoresis, 2008, 29, pp. 3024-3031. (Year: 2008).*
Cohen et al., "Correlation between Bioassay and Radioimmunoassay for Erythropoietin in Human Serum and Urine Concentrates," Proceedings of the Society for Experimental Biology and Medicine, vol. 179, 1985, pp. 296-299.
Hamasur et al., "Rapid diagnosis of tuberculosis by detection of mycobacterial lipoarabinomannan in urine," Journal of Microbiological Methods, vol. 45, 2001, pp. 41-52.
International Preliminary Report on Patentability and English translation of the Written Opinion of the International Searching Authority (Forms PCT/IB/326, PCT/IB/373 and PCT/ISA/237) for International Application No. PCT/JP2020/042911, dated Aug. 11, 2022.
International Search Report (Form PCT/ISA/210) for International Application No. PCT/JP2020/042911, dated Jan. 12, 2021, with English translation.
Rachmayati et al., "Detection of Mycobacterial Lipoarabinomannan with A Monoclonal Antibody Qualitative ELISA in Urine of Tuberculous Meningitis Patients," The Indonesian Biomedicial Journal, vol. 8, No. 1, 2016, pp. 55-60.
Vogeser et al., "Free serum cortisol: quantification applying equilibrium dialysis or ultrafiltration and an automated immunoassay system," Clin Chem Lab Med, vol. 45, No. 4, 2007, pp. 521-525.
Broger et al., "Novel lipoarabinomannan point-of-care tuberculosis test for people with HIV: a diagnostic accuracy study," The Lancet Infectious Diseases, vol. 19, Aug. 2019, pp. 852-861.
Extended European Search Report for corresponding European Application No. 20916499.5, dated Jan. 17, 2023.
Moreau, "Urine LAM detection: what is the future?," Advanced TB Diagnostics, Jun. 19, 2018, URL: <https://www.teachepi.org/wp-content/uploads/Courses/ADV-2018/E.-Moreau-LAM-Slides.pdf>, 32 pages total.

(Continued)

*Primary Examiner* — Gary Counts
(74) *Attorney, Agent, or Firm* — Birch, Stewart, Kolasch & Birch, LLP

(57) ABSTRACT

An immunochromatography includes a concentration step of concentrating a solution capable of containing an antigen by ultrafiltration to obtain an antigen-concentrated solution; a spreading step of spreading particle composite bodies on an insoluble carrier having a reaction site at which a second binding substance capable of binding to an antigen in the antigen-concentrated solution has been immobilized, in a state where the particle composite bodies which are composite bodies of the antigen and a modified particle which is a particle modified with a first binding substance capable of binding to the antigen are formed; a capturing step of capturing the particle composite bodies at the reaction site of the insoluble carrier; and an amplification step of amplifying information of the particle composite bodies captured in the capturing step.

4 Claims, 1 Drawing Sheet

(56) References Cited

OTHER PUBLICATIONS

Savolainen et al., "Modification of Clearview Tuberculosis (TB) Enzyme-Linked Immunosorbent Assay for TB Patients Not Infected with HIV," Clinical and Vaccine Immunology, vol. 20, No. 9, Sep. 2013, pp. 1479-1482.
Japanese Office Action for corresponding Japanese Application No. 2021-574476, dated Mar. 28, 2023, with English translation.
European Communication pursuant to Article 94(3) EPC for corresponding European Application No. 20 916 499.5, dated Nov. 28, 2025.

* cited by examiner

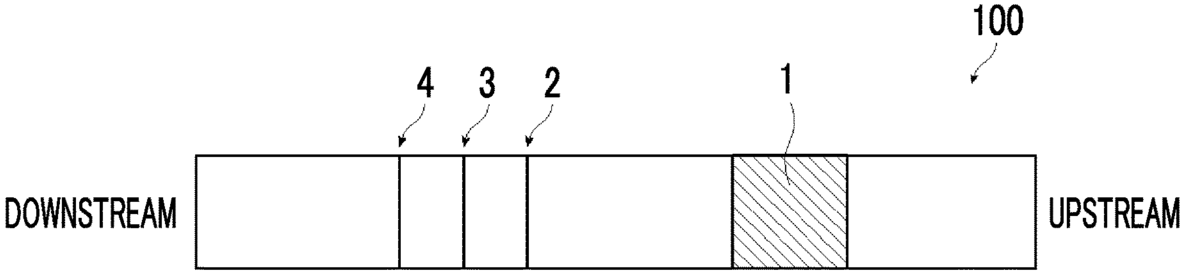
100
4
3
2
1
DOWNSTREAM
UPSTREAM

IMMUNOCHROMATOGRAPHY

CROSS-REFERENCE TO RELATED APPLICATIONS

This application is a Continuation of PCT International Application No. PCT/JP2020/042911 filed on Nov. 18, 2020, which claims priority under 35 U.S.C. § 119(a) to Japanese Patent Application No. 2020-014454 filed on Jan. 31, 2020. Each of the above application(s) is hereby expressly incorporated by reference, in its entirety, into the present application.

BACKGROUND OF THE INVENTION

1. Field of the Invention

The present invention relates to immunochromatography.

2. Description of the Related Art

Immunochromatography is frequently used these days since the operation is easy and measurement can be carried out in a short time.

For example, in a case where an antigen such as influenza virus or lipoarabinomannan (LAM) is detected by immunochromatography, the following operations are carried out.

First, in a case where a substance that serves as a label modified with an antibody, for example, a gold particle is used, a modified gold particle is prepared and mixed with a specimen containing an antigen. The modified gold particle binds to the antigen to form a particle composite body. In this state, in a case where these composite bodies are spread on an insoluble carrier having a detection line (a test line) onto which an antibody that specifically reacts with an antigen is applied, the particle composite bodies react with the antibody on the detection line and are captured, and detection is confirmed visually or in other manners.

Examples of such immunochromatography include the method disclosed in JP5728453B.

SUMMARY OF THE INVENTION

These days, an immunodiagnostic method applicable to a sample solution having an extremely low antigen concentration is desired, and regarding immunochromatography, there is also a demand for a method having higher sensitivity than the method in the related art (for example, the method disclosed in JP5728453B).

In consideration of the above circumstances, an object of the present invention is to provide immunochromatography having high detection sensitivity.

As a result of diligent studies on the above-described objects, inventors of the present invention have found that the above-described objects can be achieved by concentrating a sample solution by ultrafiltration and have reached the present invention.

That is, the inventors of the present invention have found that the object can be achieved by the following configurations.

(1) Immunochromatography comprising:

- a concentration step of concentrating a solution capable of containing an antigen by ultrafiltration to obtain an antigen-concentrated solution;
- a spreading step of spreading particle composite bodies on an insoluble carrier having a reaction site at which a second binding substance capable of binding to an antigen in the antigen-concentrated solution has been immobilized, in a state where the particle composite bodies which are composite bodies of the antigen and a modified particle which is a particle modified with a first binding substance capable of binding to the antigen are formed;
- a capturing step of capturing the particle composite bodies at the reaction site of the insoluble carrier; and
- an amplification step of amplifying information of the particle composite bodies captured in the capturing step.

(2) The immunochromatography according to (1), in which a molecular weight cut-off of an ultrafiltration membrane that is used in the ultrafiltration is 1 kDa to 10 kDa.

(3) The immunochromatography according to (1) or (2), in which the concentration step is a step of putting the solution capable of containing an antigen into an ultrafiltration instrument to carry out centrifugal separation.

(4) The immunochromatography according to any one of (1) to (3), in which the concentration step is a step of putting a part of the solution capable of containing an antigen into an ultrafiltration instrument to carry out centrifugal separation, subsequently putting a part of the solution capable of containing an antigen remained into a residual solution after filtration in the ultrafiltration instrument to further carry out the centrifugal separation, and repeating the operation.

(5) The immunochromatography according to any one of (1) to (4), in which the solution capable of containing an antigen is urine.

As described below, according to the present invention, it is possible to provide immunochromatography having high detection sensitivity.

BRIEF DESCRIPTION OF THE DRAWINGS

FIG. 1 is a schematic view illustrating an aspect of an insoluble carrier that is used in a method according to the embodiment of the present invention.

DESCRIPTION OF THE PREFERRED EMBODIMENTS

Immunochromatography according to the embodiment according to the embodiment of the present invention will be described below.

In the present specification, the numerical value range indicated by using "to" means a range including the numerical values before and after "to" as the lower limit value and the upper limit value, respectively.

In addition, in the present specification, one kind of each component may be used alone, or two or more kinds thereof may be used in combination. In a case where two or more kinds of each component are used in combination, the content of the component indicates a total content unless otherwise specified.

Further, in the present specification, "the detection sensitivity and the signal/noise ratio (the S/N ratio) are further improved" is also described as "the effects and the like of the present invention are more excellent".

The immunochromatography according to the embodiment of the present invention (hereinafter, also referred to as "the method according to the embodiment of the present invention") is immunochromatography including;

- a concentration step of concentrating a solution capable of containing an antigen by ultrafiltration to obtain an antigen-concentrated solution, a spreading step of spreading particle composite bodies on an insoluble carrier having a reaction site at which a second binding substance capable of binding to an antigen in the antigen-concentrated solution has been immobilized, in a state where the particle composite bodies which are composite bodies of the antigen and a modified particle which is a particle modified with a first binding substance capable of binding to the antigen are formed;

a capturing step of capturing the particle composite bodies at the reaction site of the insoluble carrier, and an amplification step of amplifying information of the particle composite bodies captured in the capturing step.

It is presumed that since the method according to the embodiment of the present invention has such a configuration, the above effects can be obtained. The reason for this is not clear; however, it is conceived to be as follows.

As described above, in the method according to the embodiment of the present invention, a solution capable of containing an antigen (a sample solution) is concentrated by ultrafiltration. In a case where a sample solution is concentrated by ultrafiltration, the water in the sample solution passes through the ultrafiltration membrane, whereas due to having a molecular weight of a certain degree, the antigen in the sample solution is difficult to pass through the ultrafiltration membrane, and thus the antigen in the sample solution is concentrated, which leads to the improvement of the detection sensitivity.

On the other hand, a sample solution generally contains impurities such as low molecular weight components and salts, in addition to water. From the studies by inventors of the present invention, it was found that in a case where the water in the specimen is simply volatilized, these impurities are concentrated together with an antigen, and the antigen-antibody reaction is inhibited, whereby the detection sensitivity is decreased. That is, it is known that the effect of improving the detection sensitivity by concentration cannot be sufficiently obtained.

The method according to the embodiment of the present invention is based on the above findings. That is, in the method according to the embodiment of the present invention, these impurities pass through the ultrafiltration membrane together with water since concentration is carried out by ultrafiltration. As a result, the above-described decrease in detection sensitivity hardly occurs. As a result, it is conceived that extremely high detection sensitivity is achieved.

Hereinafter, each of the steps included in the method according to the embodiment of the present invention will be described.

[Concentration Step]

The concentration step is a step of concentrating a solution capable of containing an antigen (a sample solution) by ultrafiltration to obtain an antigen-concentrated solution.

[Sample Solution]

The sample solution that is used in the concentration step is not particularly limited as long as it is a solution capable of containing an antigen. Examples of such a solution include a biological specimen, particularly a biological specimen of animal origin (particularly, of human origin) such as a body fluid (for example, blood, serum, plasma, spinal fluid, tear fluid, sweat, urine, pus, nasal mucus, or sputum), and mouthwash fluid.

The sample solution is preferably urine due to the reason that the effects and the like of the present invention are more excellent.

<Antigen>

Examples of the antigen include a fungus, a bacterium (for example, the tubercle *bacillus* or lipoarabinomannan (LAM) included in the tubercle *bacillus*), a virus (for example, an influenza virus), and a nuclear protein thereof. LAM is a major antigen in tuberculosis and a glycolipid which is a major constitutional component of the cell membrane and the cell wall.

The antigen is more preferably a virus (particularly, an influenza virus) or LAM and still more preferably LAM due to the reason that the effects and the like of the present invention are more excellent.

<Pretreatment of Sample Solution>

Regarding the sample solution, it is possible to use a sample solution as it is or in a form of an extraction solution obtained by extracting an antigen using an appropriate solvent for extraction, in a form of a diluent solution obtained by diluting an extraction solution with an appropriate diluent, or in a form in which an extraction solution has been concentrated by an appropriate method.

As the solvent for extraction, it is possible to use a solvent (for example, water, physiological saline, and a buffer solution) that is used in a general immunological analysis method, or a water-miscible organic solvent with which a direct antigen-antibody reaction can be carried out by being diluted with such a solvent.

[Ultrafiltration Membrane]

The ultrafiltration membrane that is used in the ultrafiltration is not particularly limited.

<Material>

The material of the ultrafiltration membrane is not particularly limited; however, specific examples thereof include an organic material such as cellulose, a cellulose ester, polysulfone, sulfonated polysulfone, polyether sulfone, sulfonated polyether sulfone, chlorinated polyethylene, polypropylene, polyolefin, polyvinyl alcohol, polymethyl methacrylate, polyvinylidene fluoride, or polytetrafluoroethylene, a metal such as stainless steel, and an inorganic material such as ceramics.

<Molecular Weight Cut-Off>

It is preferable that the molecular weight cut-off of the ultrafiltration membrane is smaller than the molecular weight of the antigen described above. For example, in a case where the above-described antigen is LAM (molecular weight: about 20 kDa), the molecular weight cut-off is preferably 10 kDa or less and more preferably 5 kDa or less.

The lower limit of the molecular weight cut-off is not particularly limited; however, it is preferably 0.1 kDa or more, more preferably 1 kDa or more, and still more preferably 3 kDa or more, due to the reason that the effects and the like of the present invention are more excellent.

It is noted that as described that "A plot of data with the molecular weight of the solute on the horizontal axis and the blocking rate on the vertical axis is called the molecular weight cut-off curve, and the molecular weight at which the blocking rate is 90% is called the molecular weight cut-off of the membrane." in Membrane Experiment Series, Volume III, Artificial Membrane, editors: Naofumi Kimura, Shinichi Nakao, Haruhiko Oya, and Tsutomu Nakagawa, p. 92, edited by the Membrane Society of Japan (Kyoritsu Shuppan Co., Ltd., 1993), the molecular weight cut-off is well known to those skilled in the art as an indicator that indicates the membrane performance of the ultrafiltration membrane.

[Procedure of Concentration Step]

The procedure of the concentration step is not particularly limited; however, a method of putting a sample solution into an ultrafiltration instrument having an ultrafiltration membrane and carrying out centrifugal separation to obtain a residual solution (an antigen-concentrated solution) can be mentioned. Among the above, due to the reason that the effects and the like of the present invention are more excellent, it is preferable that a part of a sample solution is put into an ultrafiltration instrument and subjected to centrifugal separation, subsequently a part of the sample solution remained is put into a residual solution after filtration in the ultrafiltration instrument to further carry out the centrifugal separation, and these operations are repeated.

[Spreading Step]

The spreading step is a step of carrying out spreading (spreading particle composite bodies) on an insoluble carrier having a reaction site at which a second binding substance capable of binding to an antigen has been immobilized, in a state where the particle composite bodies (preferably gold particle composite bodies described later) which are composite bodies of the antigen in the antigen-concentrated solution obtained in the above-described concentration step and a modified particle (preferably a modified gold particle described later) which is a particle (preferably a gold particle described later) modified with a first binding substance capable of binding to the antigen are formed.

[Capturing Step]

The capturing step is a step of capturing the particle composite bodies at the reaction site of the insoluble carrier.

[Amplification Step]

The amplification step is a step of amplifying the information of the particle composite bodies captured in the capturing step (preferably a silver amplification step described later).

[Preferred Aspect of Detection Step]

Due to the reason that the effects and the like of the present invention are more excellent, the process (hereinafter, also referred to as a "detection step") from the spreading step to the amplification step preferably includes;

- a spreading step of spreading gold particle composite bodies on an insoluble carrier having a reaction site at which a second binding substance capable of binding to an antigen in the above-described-concentrated solution obtained in the above-described concentration step has been immobilized, in a state where the gold particle composite bodies which are composite bodies of the antigen in the antigen-concentrated solution obtained in the concentration step described above and a modified gold particle which is a gold particle modified with a first binding substance capable of binding to the antigen are formed,
- a capturing step of capturing the gold particle composite bodies at the reaction site of the insoluble carrier, and
- a silver amplification step of silver-amplifying the gold particle composite bodies captured in the capturing step.

Hereinafter, each of the steps included in the above suitable aspect will be described.

[Spreading Step]

The spreading step is a step of carrying out spreading (spreading gold particle composite bodies) on an insoluble carrier having a reaction site at which a second binding substance capable of binding to an antigen in the above-described-concentrated solution obtained in the above-described concentration step has been immobilized, in a state where the gold particle composite bodies which are composite bodies of the antigen in the antigen-concentrated solution obtained in the concentration step described above and a modified gold particle which is a gold particle modified with a first binding substance capable of binding to the antigen are formed.

[Gold Particle Composite Body]

As described above, in the spreading step, first, the gold particle composite bodies which are composite bodies of the antigen in the antigen-concentrated solution obtained in the concentration step described above and a modified gold particle which is a gold particle modified with a first binding substance capable of binding to the antigen are formed.

(Modified Gold Particle)

The modified gold particle is a gold particle modified with the first binding substance capable of binding to an antigen.

(1) Gold Particle

The gold particle is not particularly limited, however, it is preferably a gold colloid particle due to the reason that the effects and the like of the present invention are more excellent.

The gold particle acts as a catalyst that reduces silver ions in the silver amplification step described later.

The particle diameter of the gold particles is preferably 500 nm or less, more preferably 300 nm or less, still more preferably 200 nm or less, and particularly preferably 150 nm or less, due to the reason that the effects and the like of the present invention are more excellent.

The lower limit of the particle diameter of the gold particles is not particularly limited; however, it is preferably 5 nm or more, more preferably 7 nm or more, and still more preferably 10 nm or more, due to the reason that the effects and the like of the present invention are more excellent.

The particle diameter can be measured with a commercially available particle diameter distribution meter or the like. As a method of measuring the particle size distribution, optical microscopy, confocal laser microscopy, electron microscopy, atomic force microscopy, static light scattering method, laser diffraction method, dynamic light scattering method, centrifugal sedimentation method, electric pulse measurement method, chromatography method, ultrasonic attenuation method, and the like are known, and apparatuses corresponding to the respective principles are commercially available. As the method of measuring a particle diameter, a dynamic light scattering method can be preferably used due to the particle diameter range and the ease of measurement. Examples of the commercially available measuring device using dynamic light scattering include NANOTRAC UPA (Nikkiso Co., Ltd.), a dynamic light scattering type particle size distribution measuring device LB-550 (HORIBA, Ltd.), and a Fiber-Optics Particle Size Analyzer FPAR-1000 (Otsuka Electronics Co., Ltd.). In the present invention, the average particle diameter is obtained as a value of a median diameter (d=50) measured at a measurement temperature of 25° C.

(2) First Binding Substance

The first binding substance is not particularly limited as long as it is capable of binding to the above-described antigen; however, due to the reason that the effects and the like of the present invention are more excellent, it is preferably a protein, more preferably an antibody (for example, a polyclonal antibody or a monoclonal antibody), and from the viewpoint of achieving higher detection sensitivity, it is still more preferably a monoclonal antibody.

The above antibody is not particularly limited. However, it is possible to use, for example, an antiserum prepared from a serum of an animal immunized with an antigen, or an immunoglobulin fraction purified from an antiserum. In addition, it is possible to use a monoclonal antibody obtained by cell fusion using spleen cells of an animal immunized with an antigen, or a fragment thereof [for example, $F(ab')_2$, Fab, Fab', or Fv]. The preparation of these antibodies can be carried out by a conventional method.

In a case where the antigen is LAM, examples of the first binding substance include the A194-01 antibody described in WO2017/139153A. The entire content disclosed in WO2017/139153A relating to the A194-01 antibody is incorporated in the present specification as a part of the disclosure of the present specification.

In a case where the antigen is LAM, other examples of the first binding substance include the antibody having a sequence described as MoAb1 in paragraph No. [0080] of WO2013/129634A. The entire content disclosed in WO2013/129634A relating to the MoAb1 antibody is incorporated in the present specification as a part of the disclosure of the present specification.

(3) Method of Manufacturing Modified Gold Particle

The method of manufacturing the modified gold particle is not particularly limited, and a known method can be used.

Examples thereof include a chemical bonding method such as a method of utilizing the fact that gold and an SH group are chemically bonded and carrying out immobilization with an Au—S bond that is generated on the Au surface when an SH bond of an antibody is cleaved in a case where the SH bond thereof approaches a gold particle.

<Insoluble Carrier>

The above-described insoluble carrier is an insoluble carrier having a reaction site (a test line) at which a second binding substance capable of binding to the above-described antigen is immobilized. The insoluble carrier may have a plurality of test lines depending on the kinds of antigens (for example, a test line for influenza A type virus and a test line for influenza B type virus). In addition, the insoluble carrier may have a control line on the downstream side of the test line in order to check the spreading of the gold particle composite bodies. Further, in a case where a reducing agent solution is used in the silver amplification step described later, a coloring reagent immobilization line may be provided on the downstream side of the test line in order to detect the reducing agent solution.

Examples of the specific aspect of the insoluble carrier include a nitrocellulose membrane 100 as illustrated in FIG. 1, which has from the upstream side; a gold colloid holding pad 1, a test line 2, a control line 3, and a coloring reagent immobilization line 4. Here, the gold colloid holding pad 1 is a pad that holds gold particles (modified gold particles) modified with the first binding substance, the test line 2 is a line on which the second binding substance is immobilized, the control line 3 is a line for checking the spreading, and the coloring reagent immobilization line 4 is a line for detecting the reducing agent solution described later. Here, the upstream side and the downstream side mean descriptions intended to indicate the spreading from the upstream side to the downstream side at the time when gold particle composite bodies are spread.

The more specific aspect of the insoluble carrier (or an immunochromatographic kit having the insoluble carrier) include, for example, the insoluble carrier or the immunochromatographic kit disclosed in JP5728453B, and the entire content of JP5728453B relating to the insoluble carrier and the immunochromatographic kit is incorporated in the present specification as a part of the disclosure of the present specification.

(Insoluble Carrier)

The insoluble carrier is preferably a porous carrier. In particular, it is preferably a nitrocellulose film (a nitrocellulose membrane), a cellulose membrane, an acetyl cellulose membrane, a polysulfone membrane, a polyether sulfone membrane, a nylon membrane, a glass fiber, a non-woven fabric, a cloth, a thread, or the like, and more preferably a nitrocellulose film, due to the reason that the effects and the like of the present invention are more excellent.

(Second Binding Substance)

The second binding substance is not particularly limited as long as it is capable of binding to the above-described antigen.

Specific examples and the suitable aspect of the second binding substance are respectively the same as those of the above-described first binding substance.

The second binding substance may be the same as or different from the above-described first binding substance; however, an aspect in which the second binding substance is a different substance is preferable due to the reason that the effects and the like of the present invention are more excellent.

In addition, in a case where the first binding substance and the second binding substance are antibodies, an aspect in which the antibody which is the first binding substance and the antibody which is the second binding substance are different from each other is preferable due to the reason that the effects and the like of the present invention are more excellent.

Further, in a case where the first binding substance and the second binding substance are antibodies, an aspect in which an epitope (a part of the antigen recognized by the first binding substance) of the first binding substance and an epitope (a part of the antigen recognized by the second binding substance) of the second binding substance are different from each other is preferable due to the reason that the effects and the like of the present invention are more excellent. The difference in epitope between antibodies can be confirmed by, for example, an enzyme-linked immunosorbent assay (ELISA).

<Spreading>

The method of spreading gold particle composite bodies on an insoluble carrier having a test line in a state where the gold particle composite bodies are formed is not particularly limited; however, examples thereof include a method in which the above nitrocellulose membrane 100 (or an immunochromatographic kit having the nitrocellulose membrane 100) as illustrated in FIG. 1 is prepared, and the antigen-concentrated solution obtained in the above-described concentration step is dropwise added onto a gold colloid holding pad and moved from the upstream side to the downstream side by using the capillary action as illustrated in FIG. 1.

[Capturing Step]

The capturing step is a step of capturing the gold particle composite bodies at the reaction site of the insoluble carrier.

As described above, since the second binding substance capable of binding to an antigen is immobilized at the reaction site of the insoluble carrier, the gold particle composite bodies (the composite bodies of an antigen and a modified gold particle) which have spread on the insoluble carrier in the spreading step is captured at the reaction site (the test line) of the insoluble carrier.

In a case where a sample solution does not contain an antigen, the above gold particle composite bodies are not formed, and thus the gold particle composite bodies are not captured at the reaction site of the insoluble carrier.

[Silver Amplification Step]

The silver amplification step is a step of silver-amplifying the gold particle composite bodies captured in the capturing step.

The silver amplification step is a step of forming large silver particles in the gold particle composite bodies captured at the reaction site of the insoluble carrier by providing silver ions to the insoluble carrier after the capturing step. More specifically, it is a step in which silver ions are reduced using gold particles of the gold particle composite bodies as a catalyst to form silver particles (for example, a diameter of 10 μm or more).

This significantly improves the detection sensitivity of the captured gold particle composite bodies.

<Suitable Aspect>

The method of providing silver ions to the insoluble carrier after the capturing step is not particularly limited; however, it is preferably a method in which the following reducing agent solution and the following silver amplification solution are used, due to the reason that the effects and the like of the present invention are more excellent.

Further, in addition to the reducing agent solution and the silver amplification solution, a washing solution may be used to wash the composite bodies remaining on the insoluble carrier except for the specific binding reaction. The reducing agent solution may also serve as a washing solution.

(Reducing Agent Solution)

The reducing agent solution contains a reducing agent capable of reducing silver ions. As the reducing agent capable of reducing silver ions, any inorganic or organic material or a mixture thereof can be used as long as it can reduce silver ions to silver. Preferred examples of the inorganic reducing agent include a reducing metal salt and a reducing metal composite body salt, of which the atomic valence is capable of being changed with a metal ion such as $Fe^{2+}$, $V^{2+}$, or $Ti^{3+}$. In a case where an inorganic reducing agent is used, it is necessary to remove or detoxify oxidized ions by chelating or reducing the oxidized ions. For example, in a system in which $Fe^{2+}$ is used as the reducing agent, a complex of $Fe^{3+}$, which is an oxide, is formed using citric acid or ethylenediaminetetraacetic acid (EDTA), and therefore detoxification is possible. In the present invention, it is preferable to use such an inorganic reducing agent. As a more preferred aspect of the present invention, it is preferable to use a metal salt of $Fe^{2+}$ as the reducing agent.

It is also possible to use, as the reducing agent, a main developing agent (for example, methyl gallate, hydroquinone, substituted hydroquinone, 3-pyrazolidones, p-aminophenols, p-phenylenediamines, hindered phenols, amidoximes, azines, catechols, pyrogallols, ascorbic acid (or derivatives thereof), or leuco dyes) that is used in a wet-type light-sensitive silver halide photographic material, and other materials obvious to those who are skilled in the technology in the present field, such as a material disclosed in U.S. Pat. No. 6,020,117A.

As the reducing agent, an ascorbic acid reducing agent is also preferable. The useful ascorbic acid reducing agent includes ascorbic acid, an analogous substance thereof, an isomer thereof, and a derivative thereof. Preferred examples thereof include D- or L-ascorbic acid and a sugar derivative thereof (for example, γ-lactoascorbic acid, glucoascorbic acid, fucoascorbic acid, glucoheptoascorbic acid, or maltoascorbic acid), a sodium salt of ascorbic acid, a potassium salt of ascorbic acid, isoascorbic acid (or L-erythroascorbic acid), a salt thereof (for example, an alkali metal salt, an ammonium salt, or a salt known in the related technical field), ascorbic acid of the enediol type, ascorbic acid of the enaminol type, ascorbic acid of the thioenol type. Particularly preferred examples thereof include D-, L-, or D,L-ascorbic acid (and an alkali metal salt thereof) or isoascorbic acid (or an alkali metal salt thereof), and a sodium salt is a preferred salt. A mixture of these reducing agents can be used as necessary.

Due to the reason that the effects and the like of the present invention are more excellent, the reducing agent solution is preferably allowed to flow so that the angle between the spreading direction in the spreading step and the spreading direction of the reducing agent solution is 0 degrees to 150 degrees, and more preferably allowed to flow so that the angle between the spreading direction in the spreading step and the spreading direction of the reducing agent solution is 0 degrees to 135 degrees.

Examples of the method of regulating the angle between the spreading direction in the spreading step and the spreading direction of the reducing agent solution include the method described in Examples of JP2009-150869A.

(Silver Amplification Solution)

The silver amplification solution is a solution containing a compound containing silver ions. As the compound containing silver ions, it is possible to use, for example, an organic silver salt, an inorganic silver salt, or a silver complex. Preferred examples thereof include silver ion-containing compounds having a high solubility in a solvent such as water, such as silver nitrate, silver acetate, silver lactate, silver butyrate, and silver thiosulfate. Silver nitrate is particularly preferable. The silver complex is preferably a silver complex in which silver is coordinated with a ligand having a water-soluble group such as a hydroxyl group or a sulfone group, and examples thereof include silver hydroxythioether.

The organic silver salt, the inorganic silver salt, or the silver complex is contained as the silver in the silver amplification solution at a concentration of 0.001 mol/L to 5 mol/L, preferably 0.005 mol/L to 3 mol/L, and more preferably 0.01 mol/L to 1 mol/L.

Examples of the auxiliary agent of the silver amplification solution include a buffer, a preservative such as an antioxidant or an organic stabilizer, and a rate regulating agent. As the buffer, it is possible to use, for example, a buffer formed of acetic acid, citric acid, sodium hydroxide, or one of salts of these compounds, or formed of tris(hydroxymethyl)aminomethane, or other buffers that are used in general chemical experiments. These buffers are appropriately used to adjust the pH of the amplification solution to an optimum pH thereof. In addition, as the antifogging agent, an alkyl amine can be used as an auxiliary agent, and a dodecyl amine is particularly preferable. In addition, a surfactant can be used for the intended purpose of improving the solubility of this auxiliary agent, and $C_9H_{19}—C_6H_4—O—(CH_2CH_2O)_{50}H$ is particularly preferable.

Due to the reason that the effects and the like of the present invention are more excellent, the silver amplification solution is preferably allowed to flow from the direction opposite to the spreading direction in the spreading step described above and more preferably allowed to flow so that the angle between the spreading direction in the spreading step and the spreading direction of the silver amplification solution is 45 degrees to 180 degrees.

Examples of the method of regulating the angle between the spreading direction in the spreading step and the spreading direction of the silver amplification solution include the method described in Examples of JP2009-150869A.

Further, a supply aspect in which the silver amplification solution is added dropwise onto the insoluble carrier from above is also preferable in order to carry out silver amplification in a short time.

EXAMPLES

Hereinafter, the present invention will be described in more detail with reference to Examples; however, the present invention is not limited thereto.

[Preparation of Sample Solution]

Lipoarabinomannan (LAM) (02249-61, Nacalai Tesque, Inc.) (an antigen) extracted from the tubercle *bacillus* was added to a urine sample obtained by pooling urine samples (BioIVT LLC) of healthy subjects to prepare a sample solution (a solution capable of containing an antigen) of a LAM concentration shown in Table 1.

Example 1

Immunochromatography of Example 1 was carried out as follows.

[Concentration Step]

2 mL of the above-described sample solution was concentrated by ultrafiltration. Specifically, a part of the sample solution was put into an Amicon (registered trade name) Ultra ultrafiltration unit (molecular weight cut-off of ultrafiltration membrane: 3 kDa, 0.5 mL) (an ultrafiltration instrument) manufactured by Merck KGaA and subjected to centrifugal separation, and then a part of the sample solution remained (a solution that had not passed through the ultrafiltration membrane of the ultrafiltration instrument) was put into a residual solution after filtration in the ultrafiltration instrument to further carry out the centrifugal separation. These operations were repeated to concentrate 2 mL of the entire sample solution described above by ultrafiltration, thereby obtaining 0.2 mL of a residual solution (a LAM-concentrated solution). As a result of subjecting the obtained LAM-concentrated solution to mass spectrometry, it was confirmed that the LAM concentration was concentrated by 10 times.

[Spreading Step]

The nitrocellulose membrane 100 as illustrated in FIG. 1 was prepared, which has from the upstream side; the gold colloid holding pad 1, the test line 2, the control line 3, and the coloring reagent immobilization line 4. The gold colloid holding pad 1 is a pad that holds gold colloids (modified gold particles) modified with an anti-LAM monoclonal antibody, the test line 2 is a line on which the anti-LAM monoclonal antibody is immobilized, the control line 3 is a line for checking the spreading, and the coloring reagent immobilization line 4 is a line for detecting the reducing agent solution in the silver amplification step described later.

The above LAM-concentrated solution was dropwise added onto the gold colloid holding pad. As a result, gold particle composite bodies, which are composite bodies of the LAM in the solution and the gold colloid particles (modified gold particles) modified with the anti-LAM monoclonal antibody, were formed. In this state, the gold particle composite bodies were spread from the upstream side toward the downstream side of the nitrocellulose membrane.

[Capturing Step]

The gold particle composite bodies which have spread in the spreading step are captured on the test line.

[Silver Amplification Step]

The silver amplification step was carried out as follows.

<Preparation of Reducing Agent Solution>

23.6 mL of an aqueous solution of 1 mol/L iron nitrate, which was produced by dissolving iron (III) nitrate nonahydrate (manufactured by FUJIFILM Wako Pure Chemical Corporation) in water, and 13.1 g of citric acid (manufactured by FUJIFILM Wako Pure Chemical Corporation) were dissolved in 290 g of water. After all of the substances were dissolved, 36 mL of nitric acid (10% by mass) was added thereto while stirring with a stirrer, 60.8 g of ammonium iron (II) sulfate hexahydrate (manufactured by FUJIFILM Wako Pure Chemical Corporation) was added thereto, and the resultant solution was used as the reducing agent solution.

<Preparation of Silver Amplification Solution>

8 mL of a silver nitrate solution (including 10 g of silver nitrate) and 24 mL of an aqueous solution of 1 mol/L iron nitrate were added to 66 g of water. Further, this solution was mixed with a solution obtained by dissolving in advance 5.9 mL of nitric acid (10% by mass), 0.1 g of dodecyl amine (manufactured by FUJIFILM Wako Pure Chemical Corporation), and 0.1 g of a surfactant $C_{12}H_{25}—C_6H_4—O—(CH_2CH_2O)_{50}H$ in 47.6 g of water, and the resultant solution was used as the silver amplification solution.

<Spreading of Reducing Agent Solution>

In the nitrocellulose membrane, the reducing agent solution prepared as described above was allowed to flow from the same direction as that of the spreading step described above (from the upstream side).

<Spreading of Silver Amplification Solution>

After the coloring reagent immobilization line was discolored, the silver amplification solution prepared as described above was allowed to flow from the direction opposite to the spreading direction (from the downstream side) in the spreading step. In this way, the gold particle composite bodies captured on the test line were silver-amplified.

[Evaluation]

The coloration of the test line was visually checked and evaluated according to the following criteria.

++: It was detected clearly.

+: It was detected faintly.

−: An increase in concentration was detected.

The results are shown in Table 1. It means that the lower the lowest LAM concentration (the minimum detection sensitivity) among the LAM concentrations of the sample solution evaluated as ++ or +, the higher the detection sensitivity.

Example 2

Immunochromatography was carried out and evaluated according to the same procedure as in Example 1, except that in the concentration step, an Amicon (registered trade name) Ultra ultrafiltration unit (molecular weight cut-off of ultrafiltration membrane: 10 kDa, 0.5 mL) manufactured by Merck KGaA was used instead of the Amicon (registered trade name) Ultra ultrafiltration unit (molecular weight cut-off of ultrafiltration membrane: 3 kDa, 0.5 mL) manufactured by Merck KGaA. The results are shown in Table 1.

Example 3

Immunochromatography was carried out and evaluated according to the same procedure as in Example 1, except that in the concentration step, an Amicon (registered trade name) Ultra ultrafiltration unit (molecular weight cut-off of ultrafiltration membrane: 100 kDa, 0.5 mL) manufactured by Merck KGaA was used instead of the Amicon (registered trade name) Ultra ultrafiltration unit (molecular weight cut-off of ultrafiltration membrane: 3 kDa, 0.5 mL) manufactured by Merck KGaA. The results are shown in Table 1.

Comparative Example 1

Immunochromatography was carried out and evaluated according to the same procedure as in Example 1 described above, except that without carrying out the concentration step, the above-described sample solution itself was used instead of the LAM-concentrated solution in the spreading step. The results are shown in Table 1.

Comparative Example 2

Immunochromatography was carried out and evaluated according to the same procedure as in Example 1, except that in the spreading step, the following LAM-concentrated solution was used instead of the LAM-concentrated solution. The results are shown in Table 1.

[LAM-Concentrated Solution Used in Comparative Example 2]

2 mL of the above-described sample solution was concentrated by freeze-drying. Specifically, 2 mL of the above-described sample solution was frozen at −80° C. for 10 hours and then freeze-dried for 24 hours using a small freeze-dryer FDS-1000 (manufactured by TOKYO RIKAKIKAI Co., LTD.). After freeze-drying, 0.2 mL of urine containing no LAM was added to obtain a LAM-concentrated solution in which the LAM concentration was concentrated by 10 times. It is noted that as a result of composition analysis, it was confirmed that impurities such as sodium phosphate were contained.

TABLE 1

| | | Example 1 | Example 2 | Example 3 | Comparative Example 1 | Comparative Example 2 |
|---|---|---|---|---|---|---|
| Concentration step | | Present | Present | Present | Absent | Freeze-drying |
| Molecular weight cut-off | | 3 kDa | 10 kDa | 100 kDa | – | – |
| LAM concentration | 0.6 ng/mL | ++ | ++ | ++ | ++ | + |
| | 0.4 ng/mL | ++ | ++ | ++ | ++ | – |
| | 0.2 ng/mL | ++ | ++ | ++ | + | – |
| | 0.1 ng/mL | ++ | ++ | ++ | – | – |
| | 0.05 ng/mL | ++ | ++ | ++ | – | – |
| | 0.03 ng/mL | ++ | ++ | ++ | – | – |
| | 0.025 ng/mL | ++ | ++ | + | – | – |
| | 0.02 ng/mL | + | + | – | – | – |
| | 0.01 ng/mL | – | – | – | – | – |
| | 0.005 ng/mL | – | – | – | – | – |

As can be seen from Table 1, Examples 1 to 3 in which concentration was carried out by ultrafiltration exhibited high detection sensitivity as compared with Comparative Example 1 in which concentration was not carried out and Comparative Example 2 in which concentration was carried out by freeze-drying. Among them, Examples 1 and 2 in which the molecular weight cut-off of the ultrafiltration membrane used in the ultrafiltration was 1 kDa to 10 kDa exhibited higher detection sensitivity.

EXPLANATION OF REFERENCES

1: gold colloid holding pad
2: test line
3: control line
4: coloring reagent immobilization line
100: nitrocellulose membrane

What is claimed is:

1. A method of immunochromatography comprising:

a concentration step of concentrating a solution capable of containing an antigen by ultrafiltration to obtain an antigen-concentrated solution, wherein the solution capable of containing an antigen is urine;

a spreading step of, by adding dropwise the antigen-concentrated solution directly onto a gold colloid holding pad, which is a pad that holds modified gold particles which are gold particles modified with a first binding substance capable of binding to an antigen in the antigen-concentrated solution, of an insoluble carrier having the gold colloid holding pad and a reaction site at which a second binding substance capable of binding to the antigen has been immobilized, spreading gold particle composite bodies on the insoluble carrier, in a state where the gold particle composite bodies which are composite bodies of the antigen and the modified gold particles are formed;

a capturing step of capturing the gold particle composite bodies at the reaction site of the insoluble carrier; and a silver-amplifying step of silver-amplifying the captured gold particle composite bodies, wherein a molecular weight cut-off of an ultrafiltration membrane that is used in the ultrafiltration is 1 kDa to 5 kDa.

2. The method of immunochromatography according to claim 1, wherein the concentration is performed by putting the solution capable of containing an antigen into an ultrafiltration instrument to carry out centrifugal separation.

3. The method of immunochromatography according to claim 1, wherein the concentration is performed by putting a part of the solution capable of containing an antigen into an ultrafiltration instrument to carry out centrifugal separation, subsequently putting a part of the solution capable of containing an antigen remained into a residual solution after filtration in the ultrafiltration instrument to further carry out the centrifugal separation, and repeating the operation.

4. The method of immunochromatography according to claim 2, wherein the concentration is performed by putting a part of the solution capable of containing an antigen into an ultrafiltration instrument to carry out centrifugal separation, subsequently putting a part of the solution capable of containing an antigen remained into a residual solution after filtration in the ultrafiltration instrument to further carry out the centrifugal separation, and repeating the operation.

* * * * *